United States Patent [19]

Matsumoto et al.

[11] 4,334,042
[45] * Jun. 8, 1982

[54] CARBONYLATION OF OLEFINIC COMPOUNDS

[75] Inventors: Mitsuo Matsumoto; Masuhiko Tamura, both of Kurashiki, Japan

[73] Assignee: Kuraray Co. Ltd., Kurashiki, Japan

[ * ] Notice: The portion of the term of this patent subsequent to Dec. 9, 1997, has been disclaimed.

[21] Appl. No.: 59,518

[22] Filed: Jul. 23, 1979

[30] Foreign Application Priority Data

Aug. 7, 1978 [JP] Japan .................................. 53-96387

[51] Int. Cl.³ .................... C07C 45/50; C07C 67/38; C08F 8/14; C08F 8/00
[52] U.S. Cl. ........................................ 525/339; 203/6; 203/38; 260/410.6; 260/410.9 R; 260/465.1; 260/465.4; 560/105; 560/155; 560/175; 560/177; 560/185; 560/187; 560/204; 560/207; 560/233; 560/266; 564/467; 568/429; 568/454; 568/909; 525/340; 525/383; 525/384
[58] Field of Search ................. 260/604 HF, 410.9 R, 260/410.6, 465.1, 465.4, 599, 602; 560/233, 266, 185, 232, 105, 155, 204, 207, 177, 114, 175, 187; 203/6, 38; 568/909, 454, 429, 453; 562/522; 525/339, 340, 384, 383; 564/467

[56] References Cited

U.S. PATENT DOCUMENTS 3,933,919  1/1976  Wilkinson .................... 260/604 HF
3,954,877  5/1976  Gipson ......................... 260/604 HF
4,238,419 12/1980  Matsumoto et al. ................ 568/454

*Primary Examiner*—Vivian Garner
*Attorney, Agent, or Firm*—Barry Kramer

[57] ABSTRACT

In the carbonylation of olefinic compounds in the presence of a cobalt carbonyl catalyst, the addition to the reaction system of a secondary phosphine oxide represented by the general formula

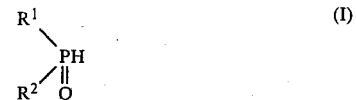

wherein $R^1$ and $R^2$ are the same or different and each is substituted or unsubstituted hydrocarbon residue having not more than about 20 carbon atoms, in an amount of 0.2 to 20 moles per gram atom of the cobalt makes it possible to separate the reaction product from the reaction mixture by direct distillation without any such special operation for the catalyst separation as required in the conventional processes. The distillation residue which contains the catalyst can be recycled for the reuse thereof in the carbonylation.

8 Claims, No Drawings

CARBONYLATION OF OLEFINIC COMPOUNDS

BACKGROUND OF THE INVENTION

1. Field of the Invention

This invention relates to a process for carbonylating olefinic compounds with the aid of cobalt carbonyl catalysts.

2. Description of the Prior Art

The reaction generally called "carbonylation," which includes the so-called hydroformylation for converting olefinic compounds into aldehydes and/or alcohols by reaction with a hydrogen/carbon monoxide gas mixture in the presence of a cobalt carbonyl catalyst and the so-called hydroesterification for converting olefinic compounds into esters by reaction with carbon monoxide and an alcohol, has so far been used widely in the industry. In this carbonylation, for example in the production of butyraldehydes from propylene, the reaction is carried out in the presence of a cobalt carbonyl catalyst under such reaction conditions as temperatures of 130°–180° C. and pressures of 100–300 atmospheres. Such high temperatures and high pressures, however, are undesirable from a commercial viewpoint because not only high cost of equipment and high cost of operation result but also formation of byproducts is significant.

In the conventional carbonylation processes using cobalt carbonyl catalysts, the products are separated from the reaction mixtures in a complicated manner; for example, prior to distillation, the cobalt carbonyl catalyst is separated from the reaction mixture in the form of metallic cobalt or a cobalt salt by steaming or by contacting with an aqueous mineral acid or an aqueous alkali solution and only thereafter the product is recovered by distillation. The reasons why which such a complicated procedure is required in separating the product from the reaction mixture are (1) that the cobalt carbonyl catalysts are unstable against heat under the conditions encountered in the distillation where the temperature is high and the carbon monoxide partial pressure is low, which makes it impossible to recycle the catalyst due to thermal decomposition of the cobalt carbonyl catalyst and deposition of metallic cobalt on the distillation vessel wall when the reaction mixture is subjected directly to distillation and (2) that, when the product aldehydes are distilled in the presence of the cobalt carbonyl catalyst, the aldehydes undergo undesirable side reactions which consequently decrease the yield of the aldehydes. Thus, the steps of separating and regenerating the catalyst are essential in the conventional processes, and so far the immediate distillation of the reaction mixture containing the catalyst has not been commercially employed. Moreover, conversion of the metallic cobalt or cobalt salt so recovered into an active cobalt carbonyl catalyst, requires severe conditions such as high temperature and high pressure. Thus, the difficulties of the principal reaction which requires high temperatures and high pressures in order to maintain the activity of the cobalt carbonyl catalyst under the conditions of carbonylation are further compounded by the catalyst regeneration process.

To reduce the instability of the cobalt carbonyl catalyst under low carbon monoxide partial pressure and also to make it possible to separate the product from the reaction mixture by distillation of the latter containing the catalyst, a method has been proposed which employs a cobalt catylst modified with a trisubstituted phosphine, typically tributylophosphine or trioctylphosphine, as can be found in the production of butyl alchol and/or 2-ethylhexanol from propylene. One example of such a method may be found in J. Organometal. Chem., 13, 469 (1968). According to this method, the reaction can be carried out under lower pressures as compared with the case of the butyraldehydes synthesis from propylene with the aid of the above-mentioned cobalt carbonyl catalyst, and moreover the reaction mixture can, in principle, be subjected to distillation without any prior treatment. However, this method using such modified cobalt catalysts is not satisfactory in respect of catalyst separation and catalyst recycling; in fact, metallic cobalt is formed by decomposition of a part of the modified cobalt catalyst at the time of separation of the product from the reaction mixture and is deposited in the separation vessel or later, and part of the cobalt catalyst may accompany the distillate.

In view of the above, it is no exaggeration to say that the carbonylation of olefinic compounds with the aid of cobalt carbonyl catalysts, viewed from an industrial standpoint is brought with difficulty because of the problems of: (1) separation of cobalt catalysts from the reaction mixture, (2) reuse of the catalysts by recycling, and (3) the severity of the reaction conditions inevitably brought thereby.

SUMMARY OF THE INVENTION

It has now been found that the above problems can be solved in accordance with the present invention in a very simple manner by carrying out the carbonylation of olefinic compounds in the presence of a cobalt carbonyl catalyst plus a secondary phosphine oxide represented by the general formula (I):

wherein $R^1$ and $R^2$ are the same or different and each is a substituted or unsubstituted hydrocarbon residue having not more than about 20 carbon atoms, added to the reaction system in an amount of 0.2 to 20 moles per gram atom of the cobalt. According to the invention, the reaction product can be separated from the reaction mixture by distillation of the reaction mixture as it is, without any special catalyst separation procedure, and the distillation residue containing the catalyst as it is can be recycled and reused in the carbonylation process. Moreover, the cobalt carbonyl catalyst so recycled can exhibit satisfactory catalytic activity under relatively mild reaction conditions, and therefore the carbonylation conditions can be milder than those in the conventional processes.

DETAILED DESCRIPTION OF THE INVENTION

Concerning the secondary phosphine oxide represented by general formula (I), $R^1$ and $R^2$ are the same or different and each is a substituted or unsbustituted hydrocarbon residue having not more than about 20 carbon atoms. The hydrocarbon residue may be, for example, a saturated aliphatic hydrocarbon residue such as methyl, ethyl, propyl, butyl, pentyl, hexyl, heptyl, octyl, nonyl, decyl or dodecyl, an aromatic hydrocarbon residue such as phenyl, tolyl, ethylphenyl or xylyl, or an alicyclic hydrocarbon residue such as cyclohexyl or methylcyclohexyl. The substituted hydrocarbon residue may have one or more hetero atoms and/or hetero-atom-containing groups, which can neither act as poisons against the cobalt carbonyl catalyst nor cause any undesirable side reactions. Examples of such atoms and groups are fluorine atoms, lower alkoxy groups, hydroxyl groups and amino groups, and the hetero atom or hetero-atom-containing groups will preferably be a member selected from this group.

The following are examples of said secondary phosphine oxide represented by general formula (I):

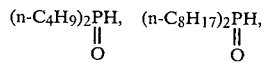

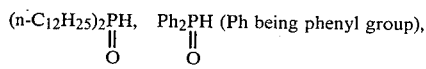

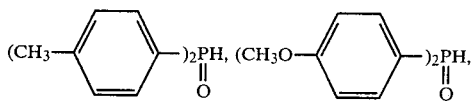

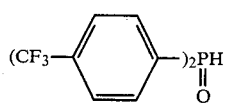

It is not clear in what state the secondary phosphine oxide exists in the reaction system. According to Tetrahedron, 23, 1065 (1967), however, it is known that secondary phosphine oxides are in tautomeric relation to phosphinous acids and the equilibrium is favorable to the left side (keto form) (see the equation below).

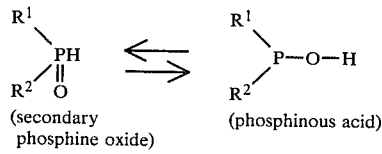

The secondary phosphine oxides of general formula (I) used according to the present invention are generally prepared according to conventional methods. However, it is also possible to either: prepare the secondary phosphine oxide of general formula (I) in a separate preparation vessel and supply the same to the carbonylation vessel without isolation thereof, or prepare the secondary phospine oxide of general formula (I) in situ in the carbonylation reaction system or in the distillation step for product separation. Preferable examples of organophosphorus compounds to be used in said in situ catalyst preparation are: (a) organophosphorus compounds represented by the general formula (II)

wherein $R^1$ and $R^2$ are as defined above, $R^3$ is a hydrogen atom or hydrocarbon residue having not more than about 20 carbon atoms and $R^4$ is a hydrocarbon residue having not more than about 20 carbon atoms; (b) secondary phosphines represented by the general formula (III)

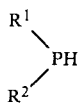

wherein $R^1$ and $R^2$ are as defined above; and (c) phosphinites of the general formula (IV)

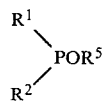

wherein $R^1$ and $R^2$ are as defined above and $R^5$ is saturated aliphatic hydrocarbon residue.

The organophosphorus compounds represented by general formula (II), on thermal decomposition, give, as is known e.g. from J. Amer. Chem. Soc., 79, 424 (1957), the corresponding secondary phosphine oxides and aldehydes or ketones in accordance with the equation (A) shown below:

$$\begin{array}{c} R^1 \\ \diagdown \\ P-C \\ \diagup \| \phantom{x} | \diagdown \\ R^2 \phantom{x} O \phantom{x} OH \phantom{x} R^4 \end{array} \underset{\Delta}{\rightleftarrows} \begin{array}{c} R^1 \\ \diagdown \\ PH \\ \diagup \| \\ R^2 \phantom{x} O \end{array} + O=C\begin{array}{c} R^3 \\ \diagdown \\ \\ \diagdown \\ R^4 \end{array} \quad (A)$$

(II)                    (I)

Thus, the above organophosphorus compounds (II) give to various extents, depending on the kinds of $R^1$, $R^2$, $R^3$ and $R^4$, the corresponding phosphine oxides of general formula (I) at temperatures generally employed for the carbonylation or for the product separation by distillation. The secondary phosphines of general formula (III) are, as is known, e.g., from J. Org. Chem., 26, 4626 (1961), susceptible to oxidation by oxygen and are converted into the corresponding phosphine oxides in accordance with the following equation (B):

$$\begin{array}{c} R^1 \\ \diagdown \\ PH \\ \diagup \\ R^2 \end{array} + \tfrac{1}{2} O_2 \longrightarrow \begin{array}{c} R^1 \\ \diagdown \\ PH \\ \diagup \| \\ R^2 \phantom{x} O \end{array} \quad (B)$$

(III)                (I)

The phosphinites of general formula (IV) are, as is known, e.g. from G. M. Kosolapoff and L. Maier, Organic Phosphorus Compounds, Vol. 4, John Wiley & Sons, Inc. (1972), page 497, easily hydrolyzed in the presence of water to give the corresponding secondary phosphine oxides in accordance with the following equation (C):

$$\begin{array}{c} R^1 \\ \diagdown \\ POR^5 \\ \diagup \\ R^2 \end{array} + H_2O \longrightarrow \begin{array}{c} R^1 \\ \diagdown \\ PH \\ \diagup \| \\ R^2 \phantom{x} O \end{array} + R^5OH \quad (C)$$

(IV)                    (I)

Therefore, in practicing the present invention, the organophosphorus compound of general formula (II), the secondary phosphine of general formula (III) or the phosphinite of general formula (IV) can act as a substitute for the secondary phosphine oxide of general formula (I). Thus, the secondary phosphine oxide can be prepared in situ during the carbonylation or in the step of product separation by distillation by adding the above-mentioned compound (II, III or IV) to the reaction or distillation system, and in this case, too, the same effect can be achieved as the addition of the secondary phosphine oxide of general formula (I).

Concerning general formula (II), as $R^3$ may be mentioned, in addition to hydrogen atom, such saturated aliphatic hydrocarbon residues as methyl, ethyl, propyl, butyl, pentyl, hexyl, heptyl, octyl, nonyl, decyl and dodecyl, such aromatic hydrocarbon residues as phenyl, tolyl, ethylphenyl and xylyl, and such alicyclic hydrocarbon residues as cyclohexyl and methylcyclohexyl. There may be mentioned as $R^4$ such saturated aliphatic hydrocarbon residues as methyl, ethyl, propyl, butyl, pentyl, hexyl, heptyl, octyl, nonyl, decyl and dodecyl, such aromatic hydrocarbon residues as phenyl, tolyl, ethylphenyl and xylyl, and such alicyclic hydrocarbon residues as cyclohexyl and methylcyclohexyl.

In general formula (IV), $R^5$ is a saturated aliphatic hydrocarbon residue preferably having not more than about 20 carbon atoms, such as methyl, ethyl, propyl, butyl, pentyl, hexyl or octyl.

It is necessary that the secondary phosphine oxide of general formula (I) be present in the reaction system in an amount of 0.2 to 20, preferably 0.5 to 5 moles per gram atom of cobalt. In case the amount is less than 0.2 mole, any substantial effect of inhibiting the decomposition of cobalt carbonyl catalysts cannot be produced in the steps of carbonylation and of separation of the product from the reaction mixture by distillation. Conversely, if the amount exceeds 20 moles, the rate of carbonylation is unfavorably decreased.

The same applies to the amounts to be added of the organophosphorus compound of general formula (II), the secondary phosphine of general formula (III) and the phosphinite of general formula (IV).

The cobalt carbonyl catalysts to be used in accordance with the invention may be those cobalt carbonyl complexes that have so far been known. Specifically, there may be mentioned such cobalt carbonyl complexes as $HCo(CO)_4$, $Co_2(CO)_8$ and $Co_4(CO)_{12}$ and modified cobalt complexes represented by the general formula $[Co(CO)_3L]_2$ wherein L is such ligand as trisubstituted phosphine (e.g. tributylphosphine, trioctylphosphine, tridecylphosphine, tribenzylphosphine) or organic nitrogen ligand (e.g. pyridine, picoline). Such cobalt compounds as cobalt carbonate, cobalt acetylacetonate, cobalt acetate and cobalt octanoate also give cobalt carbonyl complexes under the reaction conditions and act as cobalt carbonyl catalyst species. Consequently, when these cobalt compounds are fed to the reaction vessel, the same effect as that of feeding cobalt carbonyl complexes can be produced. It is also possible to provide a separate vessel for catalyst preparation, synthesize therein a cobalt carbonyl complex from the above-mentioned cobalt compound in a conventional manner and feed the liquid reaction mixture as it is to the carbonylation reaction vessel. The concentration of the cobalt carbonyl catalyst in the reaction system is generally selected from he range of 0.0001 to 0.1 mole per mole of the olefinic compound charged, depending upon the reaction conditions, kind of the catalyst, presence or absence of (excess) ligand, and so forth. When a modified cobalt catalyst is used for the carbonylation, the amount of the ligand is preferably about 0.5 to 5 moles per gram atom of cobalt.

Specific examples of olefinic compounds to which the process of the present invention is advantageously applicable are ethylene, propylene, 1-butene, isobutylene, 1-hexene, 1-octene, 2-octene, diisobutylene, isobutylene-1-butene codimer, 3-decene, 1-dodecene, 1-hexadecene, 1,11-dodecadiene, Ziegler process alpha-olefins, propylene trimer, propylene tetramer, olefins from paraffin oxidation processes, olefins from wax decomposition processes, and other straight chain or branched olefinic hydrocarbons, styrene, acrylonitrile, vinyl ethyl ether, dimethylallylamine, vinyl acetate, allyl acetate, methyl acrylate and other substituted olefins.

The reaction is generally conducted in an organic solvent in the presence of the cobalt carbonyl catalyst and the secondary phosphine oxide of general formula (I).

No limitation is imposed upon the organic solvent to be used in the carbonylation of the invention, provided that it can dissolve the cobalt carbonyl catalyst but cannot produce any adverse effect on the carbonylation reaction. Industrially, the starting olefinic compound, the product aldehydes and/or alcohols, and the high boiling byproducts, alone or in combination, may also serve as the reaction solvent. Other preferable examples of the reaction solvent are especially aromatic hydrocarbons such as benzene, toluene, xylene and dodecylbenzene, alicyclic hydrocarbons such as cyclohexane, ethers such as dibutyl ether, ethylene glycol dimethyl ether, diethylene glycol diethyl ether, tetraethylene glycol dimethyl ether and tetrahydrofuran, and esters such as diethyl phthalate and dioctyl phthalate. In selecting the solvent, some physical constants, e.g. differences in boiling points among the starting material, reaction product and solvent, are of course taken into consideration.

Illustrative of the alcohols which can give esters by reaction with olefinic compounds in accordance with the invention, are for example, methanol, ethanol, butanol, ethylene glycol, trimethylolpropane and pentaerythritol. The above-mentioned straight chain or branched olefinic hydrocarbons may be used in this case, too.

The applicable reaction temperature is, as in the case of the conventional carbonylation with the cobalt carbonyl catalyst, in the range of 100°–200° C., preferably 130°–180° C. The composition of the gas mixture for the reaction is quite the same as has been used in the conventional carbonylation processes.

The reaction pressure may generally be selected in the range between about 30 and about 300 atmospheres. However, since the catalyst is stabilized when the process of the invention is employed, the reaction can be carried out also at much lower pressures.

In the separation of reaction products from the reaction mixture by distillation, the temperature of the liquid phase in the distillation column or vessel is important with respect to separation efficiency and possibility of recycling of the catalyst components, and it is desirable to adjust the pressure so that said temperature may fall under the range of 50°–200° C., preferably 80°–180° C. The distillation residue remaining after separation of the reaction products from the reaction mixture and containing the catalyst components is for the most part recycled directly to the carbonylation process for reuse. Preferably, however, a part (e.g. several percent) of said distillation residue is taken out separately so as to remove high-boiling byproducts.

Commercially, the carbonylation of the invention is carried out in a reaction vessel equipped with a stirrer or in a columnar reaction vessel either continuously or batchwise. As the catalyst components recycled according to the process of the invention can show excellent catalytic activity even at relatively low pressures, the process of the invention has an advantage from an industrial standpoint that the reaction pressure can be lowered to a great extent as compared with the prior art processes, and therefore it may be said that the significance of the present invention in the industry is very great.

The following examples will illustrate the invention in more detail. However, they are not limitative of the invention by any means.

In the following examples and examples for comparison, each carbonylation reaction was conducted in a 500-ml stainless steel autoclave equipped with thermometer, magnetic stirrer, gas inlet, reflux condenser and gas outlet. The autoclave was connected with an external gas reservoir (filled with a gas having the same composition as that of the gas to be charged to the autoclave) via a pressure adjusting valve so that the portion of the gas that had been consumed in the reaction might be supplemented and consequently the pressure might be maintained at a constant level during the reaction.

EXAMPLE 1

The autoclave was charged with a dodecylbenzene solution (125 ml) containing 0.60 millimole of $Co_2(CO)_8$ and 3.6 millimoles of $(n-C_8H_{17})_2P(=O)H$, and 0.40 mole of 1-decene. The reaction was carried out at a pressure of an $H_2/CO$ (molar ratio being 1/1) gas mixture of 70 kg/cm$^2$ (absolute pressure) at 150° C. for 4 hours with vigorous stirring. A very small amount of the liquid reaction mixture was taken out and analyzed by gas chromatography, which revealed that 12 millimoles of 1-decene was remaining unreacted, the conversion of 1-decene being 97%, and the yields of undecylaldehydes and undecyl alcohols were 329 millimoles and 27 millimoles, respectively.

After the reaction, the autoclave contents were cooled to 130° C., while the gas was discharged (depressurization). The whole amount of the effluent gas was led to a toluene trap cooled in an acetone-dry ice bath. The unreacted starting material and the reaction products were distilled off at the same temperature (130° C.) over an hour while varying the degree of vacuum according to the distilling rate.

A very small amount of the distillation residue in the autoclave was taken and analyzed by gas chromatography, which showed that 16 millimoles of undecylaldehydes and 3 millimoles of undecyl alcohols were remaining.

The autoclave was charged further with 0.40 mole of 1-decene, and the reaction was repeated under the same conditions for 4 hours. Analysis of the liquid reaction mixture showed that 20 millimoles of 1-decene was remaining unreacted (the conversion of 1-decene thus being 95%), and that the yield of undecylaldehydes was 339 millimoles and that of undecyl alcohols 32 millimoles. The liquid reaction mixture appeared homogeneous and deposition of metallic cobalt could not be detected.

Example for Comparison 1

The hydroformylation of 1-decene was conducted under the same conditions as in Example 1 except that the addition of $(n-C_8H_{17})_2P(=O)H$ was omitted. Analysis of the liquid reaction mixture revealed that the conversion of 1-decene was 100%, the yield of undecylaldehydes 323 millimoles and the yield of undecyl alcohols 40 millimoles. Then the reduced pressure distillation was made under the same conditions as in Example 1, then 0.40 mole of 1-decene was added and the reaction repeated. Analysis of the liquid reaction mixture showed that 188 millimoles of 1-decene was remaining unreacted, the conversion of 1-decene thus being 53%, and that the yield of undecylaldehydes and that of undecyl alcohols were only 121 and 11 millimoles, respectively. In this case, 64 millimoles of 2-decene was formed by isomerization of 1-decene. Moreover, a considerable amount of metallic cobalt was found as a precipitate in the liquid reaction mixture.

As is clear from Example 1 and Example for Comparison 1, the addition of the secondary phosphine oxide in accordance with the present invention does not cause any substantial decrease in catalytic activity even after the distillation operation.

EXAMPLE 2

The hydroformylation of diisobutylene and the subsequent distillation were repeated under the same conditions as in Example 1, using, however a solution of 0.60 millimole of $Co_2(CO)_8$ and 3.0 millimoles of $(n-C_8H_{17})_2P(=O)-CH(OH)CH_2CH_2CH_3$ in 70 ml of dioctyl phthalate plus 70 ml of dodecylbenzene, and 0.40 mole of diisobutylene (terminal olefin content 87%) and employing a reaction pressure of 100 kg/cm$^2$ (absolute pressure).

The conversions of diisobutylene in the first and the second run were 84% and 84%, respectively, the yeilds of isononylaldehyde 267 and 271 millimoles, respectively, and the yields of isononyl alcohol 24 and 28 millimoles, respectively.

EXAMPLE 3

The reaction was conducted at a pressure of an $H_2/CO$ (molar ratio being 2/1) gas mixture of 60 kg/cm$^2$ (absolute pressure) at 175° C. for 5 hours, using a solution of 2.0 millimoles of $Co_2(CO)_8$, 8.0 millimoles of trioctylphosphine and 2.0 millimoles of $(C_6H_5)_2P(=O)H$ in 100 ml of dioctyl phthalate, and 0.80 mole of 1-hexene. The liquid reaction mixture, after analysis thereof, was subjected to distillation in the same manner as in Example 1. A 10 ml sample of the distillation residue was taken, and thereafter 10 ml of the dioctyl phthalate solution containing $Co_2(CO)_8$, trioctylphosphine and $(C_6H_5)_2P(=O)H$ at the same concentrations as above, and 0.80 mole of 1-hexene were added to the autoclave, and the hydroformylation was repeated. In this manner, 10 runs in all of the hydroformylation of 1-hexene were repeated. The conversions of 1-hexene in the first, fifth and tenth run were 96%, 94% and 91%, respectively.

The procedure of Example 3 was followed under the same conditions as in Example 3, omitting, however, the addition of $(C_6H_5)_2P(=O)H$. In this case, the conversions of 1-hexene in the first, fifth and tenth run were 97%, 90% and 80%, respectively.

EXAMPLE 4

Two runs of the hydroformylation of 2-octene were carried out under the same conditions as in Example 1, except that a solution of 0.60 millimole of $Co_2(CO)_8$ and 1.8 millimoles of $(C_6H_5)_2POC_2H_5$ in 160 ml of tetraethylene glycol dimethyl ether, and 0.24 mole of 2-octene. The conversions of 2-octene in the first and second run were 97% and 95%, respectively.

EXAMPLE 5

The autoclave was charged with a solution of 2.0 millimoles of $Co_2(CO)_8$, 10 millimoles of pyridine and 4.0 millimoles of $(C_6H_5)_2P(=O)H$ in 120 ml of dodecylbenzene, together with 0.30 mole of 1-pentene and 1.2 moles of methanol, and the hydroesterification of 1-pentene with methanol was carried out at 150° C. at a carbon monoxide pressure of 80 kg/cm² (absolute) and at a hydrogen pressure of 8 kg/cm² (absolute) for 6 hours. The liquid reaction mixture, after analysis thereof, was subjected to distillation in the same manner as in Example 1. Then, 6.0 millimoles of pyridine, 0.30 mole of 1-pentene and 1.2 moles of methanol were added to the autoclave, and the hydroesterification was repeated under the same conditions as above. The conversions of 1-pentene in the first and the second run were 95% and 94%, respectively, and the yields of methyl hexanoate were 228 and 226 millimoles, respectively.

The procedure of Example 5 was repeated under the same conditions as in Example 5, without the addition of $(C_6H_5)_2P(=O)H$, however. The conversions of 1-pentene in the first and the second run were 97% and 47%, respectively.

EXAMPLE 6

Using a solution of 0.60 millimole of $Co_2(CO)_8$ and 3.6 millimoles of $(n\text{-}C_8H_{17})_2P(=O)H$ in 170 ml of dodecylbenzene, and 0.40 mole of propylene, the reaction was carried out at 150° C. at a pressure of an $H_2/CO$ gas mixture (molar ratio being 1/1) of 65 kg/cm² for 4 hours. After analysis of the liquid reaction mixture, the autoclave was cooled to 120° C. (inner temperature). The same kind of trap as in Example 1 was connected to the autoclave and, after depressurization, the product was driven off by passing an $H_2/CO$ gas mixture (molar ratio 1/1) at a rate of 15 liters/hour with stirring. After analysis of the residue, 0.40 mole of propylene was again added to the autoclave and the hydroformylation repeated under the same conditions. In this manner, three runs in total of the hydroformylation of propylene were conducted. The yields of butyraldehydes in the first, the second and the third run were 337, 336 and 340 millimoles, respectively.

The procedure of Example 6 was repeated under the same conditions as in Example 6, except that the addition of $(n\text{-}C_8H_{17})_2P(=O)H$ was omitted. The yield of butyraldehydes in the second run was only 132 millimoles.

What is claimed is:

1. A process for carbonylating olefinic compounds which comprises bringing an olefinic compound into contact with carbon monoxide and hydrogen or an alcohol in the presence of a cobalt carbonyl catalyst plus a secondary phosphine oxide having the general formula (I)

wherein $R^1$ and $R^2$ are the same or different and each is a substituted or unsubstituted hydrocarbon residue containing not more than about 20 carbon atoms, said secondary phosphine oxide being added to the reaction system in an amount of 0.2 to 20 moles per gram atom of the cobalt.

2. A process as claimed in claim 1, wherein the residues $R^1$ and $R^2$ are each a hydrocarbon residue selected from the group consisting of saturated aliphatic, aromatic and alicyclic hydrocarbon residues, said hydrocarbon residue may be substituted by one or more hetero atoms or hetero-atom-containing groups selected from the group consisting of fluorine atoms, lower alkoxy groups, hydroxyl groups and amino groups.

3. A process as claimed in claim 1, wherein said secondary phosphine oxide of general formula (I) is used in an amount of 0.5 to 5 moles per gram atom of cobalt.

4. A process as claimed in claim 1, wherein the reaction pressure is about 30 to about 300 atmospheres.

5. A process as claimed in claim 1, wherein the reaction temperature is 100°–200° C.

6. A process as claimed in claim 5, wherein the reaction temperature is 130°–180° C.

7. A process as claimed in claim 1, wherein the concentration of said cobalt carbonyl catalyst in the reaction system is 0.0001–0.1 mole per mole of said olefinic compound charged.

8. A process as claimed in claim 1, wherein the unreacted starting material and the product are separated from the reaction mixture after the carbonylation by distillation and the residue which contains the catalyst components is recycles to the carbonylation reaction step.

* * * * *